US009487771B2

(12) United States Patent
Sabala et al.

(10) Patent No.: US 9,487,771 B2
(45) Date of Patent: Nov. 8, 2016

(54) **METHOD OF PEPTIDE HYDROLYSIS, PEPTIDASE, THE COMPOSITION FOR USE AS A BACTERIOSTATIC AND BACTERICIDAL AGENT, A KIT AND THE USES OF THE ACTIVE FORM OF LYTM FROM *S. AUREUS* OR DERIVATIVES THEREOF**

(71) Applicant: MIEDZYNARODOWY INSTYTUT BIOLOGII MOLEKULARNEJ I KOMORKOWEJ, Warsaw (PL)

(72) Inventors: Izabela Sabala, Skierniewice (PL); Matthias Bochtler, Piaseczno (PL)

(73) Assignee: MIEDZYNARODOWY INSTYTUT BIOLOGII MOLEKULARNEJ I KOMORKOWEJ, Warsaw (PL)

( * ) Notice: Subject to any disclaimer, the term of this patent is extended or adjusted under 35 U.S.C. 154(b) by 129 days.

(21) Appl. No.: 14/056,432

(22) Filed: Oct. 17, 2013

(65) Prior Publication Data

US 2014/0044698 A1    Feb. 13, 2014

Related U.S. Application Data

(63) Continuation-in-part of application No. PCT/PL2012/000026, filed on Apr. 18, 2012.

(30) Foreign Application Priority Data

Apr. 19, 2011    (PL) .......................................... 394619

(51) Int. Cl.
  *C12N 9/80*    (2006.01)
  *C12N 9/52*    (2006.01)
  (Continued)

(52) U.S. Cl.
  CPC ................ *C12N 9/80* (2013.01); *A01N 63/00* (2013.01); *A61K 38/4886* (2013.01); *C12N 9/52* (2013.01); *C12Y 304/24075* (2013.01); *C07K 2319/50* (2013.01)

(58) Field of Classification Search
  None
  See application file for complete search history.

(56) References Cited

U.S. PATENT DOCUMENTS 4,734,362 A * 3/1988 Hung et al. .................. 435/68.1
5,270,176 A * 12/1993 Dorschug et al. ........... 435/69.7
(Continued)

FOREIGN PATENT DOCUMENTS

WO    WO 2007/130655    11/2007
WO    WO 2010/092333    8/2010

OTHER PUBLICATIONS

Bardelang et al., "Design of a polypeptide FRET substrate that facilitates study of the antimicrobial protease lysostaphin", Biochemical Journal, vol. 418, pp. 615-624, 2009.*
(Continued)

*Primary Examiner* — Robert Mondesi
*Assistant Examiner* — Richard Ekstrom
(74) *Attorney, Agent, or Firm* — Vedder Price P.C.; Thomas J. Kowalski; Deborah L. Lu

(57) ABSTRACT

The invention relates to new method of peptide hydrolysis, in particular of the cell walls of Gram-positive bacteria, wherein the active form of LytM or derivative thereof is contacted with a peptide substrate, preferably with the cell walls of Gram-positive bacteria, in an aqueous environment of conductivity lower than 10 mS/cm. The invention also relates to composition comprising active form of LytM or derivative thereof and new uses of active form of LytM or derivative thereof.

22 Claims, 6 Drawing Sheets

(51) Int. Cl.
*A61K 38/48* (2006.01)
*A01N 63/00* (2006.01)

(56) References Cited

U.S. PATENT DOCUMENTS

2009/0130185 A1* 5/2009 Coote et al. .......... 424/445
2011/0177521 A1* 7/2011 Henkhaus .......... 435/6.15

OTHER PUBLICATIONS

Kumar, "Lysostaphin: an antistaphylococcal agent", Applied Microbiology and Biotechnology, vol. 80, pp. 555-561, 2008.*

M. Firczuk, et al., Crystal Structures of Active LytM, J. Mol. Biol. (2005) vol. 354, p. 578-590.
A. Kelly, et al., Low-Conductivity Buffers for High-Sensitivity NMR Measurements, J. Am Chem. Soc. (2002) vol. 124, p. 12013-12019.
S. G. Odintsov, et al., Latent LytM at 1.3 Å Resolution, J. Mol. Biol. (2004) vol. 335, p. 775-785.
L. Ramadurai, et al., Characterization of a Chromosomally encoded Glycylglycine Endopeptidase of *Staphylococcus aureus,* Microbiology (1999) vol. 145, p. 801-808.
I. Sabala, et al., Anti-Staphylococcal Activities of Lysostaphin and the LytM Catalytic Domain, BMC Microbiology (2012) vol. 12, No. 1, p. 1-16.

* cited by examiner

METHOD OF PEPTIDE HYDROLYSIS, PEPTIDASE, THE COMPOSITION FOR USE AS A BACTERIOSTATIC AND BACTERICIDAL AGENT, A KIT AND THE USES OF THE ACTIVE FORM OF LYTM FROM *S. AUREUS* OR DERIVATIVES THEREOF

RELATED APPLICATIONS AND INCORPORATION BY REFERENCE

This application is a continuation-in-part application of international patent application Serial No. PCT/PL2012/000026 filed Apr. 18, 2012, which published as PCT Publication No. WO 2012/144912 on Oct. 26, 2012, which claims benefit of Polish patent application Serial No. P 394619 filed Apr. 19, 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a method of peptide hydrolysis and a peptidase capable of cleaving the cell walls of Gram-positive bacteria, the composition for use as a bacteriostatic and bactericidal (e.g. as bacteriolytic) agent and uses thereof, to the kit to lyse Gram-positive bacteria and uses of the active form of LytM from *S. aureus* or derivatives thereof.

BACKGROUND OF THE INVENTION

Infections caused by Staphylococci, in particular *Staphylococcus aureus*, are increasingly difficult to treat due to rapidly emerging drug resistance. For this reason it is important not only to develop new therapies to combat staphylococcal infections, to eliminate the germ carrier, in particular among medical staff, but also to design more efficient methods of eliminating this bacteria from the environment, including hospitals. One such novel approach is the lysis of bacterial cells using lytic enzymes.

There are known peptidoglycan hydrolases, such as lysostaphin and LytM which cleave the characteristic pentaglycine cross-bridges in peptidoglycan of *Staphylococcus*, e.g. *S. aureus* and are, therefore, of interest as potential anti-staphylococcal agents.

Lysostaphin is a bacteriocin secreted by *Staphylococcus simulans* biovar *staphylolyticus*. The mature protein is inactive against the producer organism but highly effective in cleaving *S. aureus* cell walls.

Mature lysostaphin is a monomeric protein with optimal activity at temperatures about 37-40° C., pH 7.5 and has an isoelectric point pI of 9.5 (Browder H. P. et al., 1965, Biochem. Biophys. Res. Commun., 19:383-389 and Iversen O. et al., 1973, Eur. J. Biochem., 38:293-300). Lysostaphin has been used to disrupt *S. aureus* and *S. epidermidis* biofilms on artificial surfaces and has also been tested as a coating for catheters. In a mouse model, lysostaphin has been used to eradicate *S. aureus* biofilms from a catheterized jugular vein and also for treatment of systemic infections. In a cotton rat model, a lysostaphin cream has proven effective in eradicating *S. aureus* nasal colonization. In humans, lysostaphin has been used on an experimental basis to treat methicillin-resistant *S. aureus* aortic valve endocarditis.

*Staphylococcus*, in particular *S. aureus* can often cause food poisoning due to production of thermostable peptidic enterotoxins leading to intoxication. Due to the large scale of food production, the use of enzymes destroying staphylococcal cells to improve the microbiological quality of food is possible only if such enzymes are easily accessible and inexpensive. Moreover, staphylolytic enzymes used in food industry should be effective in a wide range of temperatures, in particular in low temperature regimes of food storage and during the production process, as well as maintaining their activity in low salt concentration i.e. in water, which is used to remove bacteria from production pipeline installations and other surfaces. Lysostaphin available on the market does not fulfill such demands.

There are known methods of bacterial cell lysis or of damaging bacterial cell walls that necessitate the disintegration of the cell wall structure by specific bacterial enzymes. This is particularly true for Gram-positive bacteria because of the particular structure of their cell walls. For example lysostaphin is used to lyse *S. aureus* cells. The known cell lysis methods require the reaction to be conducted in conditions resembling physiological conditions and performed in elevated temperatures of about 30-37° C. In such conditions, the isolated cell components, such as proteins or nucleic acids, can be degraded by the released enzymes, which activity is usually the highest in physiological conditions. Such degradation could be avoided if the effective cell lysis could be carried out in nonphysiological conditions, such as low concentration of salt or a wide range of temperatures, in particular in low temperatures. There are known kits containing lysostaphin which are used to isolate protoplasts, enzymes, proteins, cell components or nucleic acids from Gram-positive bacteria, e.g. from *Staphylococcus* species.

LytM is an autolysin produced by *S. aureus*. The gene of LytM from *S. aureus* was cloned and sequenced (Ramadurai L. et al., 1997, J. Bacteriol. 179:3625-31). The protein is synthesized with a signal peptide ($LytM_{1-25}$), followed by an N-terminal domain that has no similarity to the N-terminal domain of lysostaphin. The C-terminal domain of LytM can be divided into an occluding region and a region of high similarity to the lysostaphin catalytic domain. The analysis of LytM structure suggests that the full length LytM cannot have significant activity, because the active site is occluded while the catalytic domain alone should be more active than the full length protein. It is known that the cell walls of the Gram-positive bacteria differ in the number and form of amino acids present in the interpeptide bridges of the peptidoglycans. Glycylglycine endopeptidases may require certain number of glycines in the interpeptide bridges they cleave. It has been shown that $LytM_{185-316}$ cleaves tetra- and pentaglycine but not a triglycine (Firczuk M. et al., 2005, J. Mol. Biol. 354:578-590, Odintsov S. G. et al., 2004, J Mol Biol 335:775-8).

According to Bardelang et al. (2009, Biochem. J. 418:615-624), LytM can cleave not only peptidoglycans or peptides but also proteins.

The recombinant proteins are in most cases produced as fusion proteins with attached tags (peptide or protein) simplifying their subsequent purification. However, after purification the presence of such tags is undesirable. Therefore, it is necessary to cleave off such tags using a specific protease. Such enzyme has to be very efficient but also highly specific to avoid undesirable cleavage of the protein. The most commonly used proteases are: Factor Xa, PreScision and TEV proteases. They are rather expensive and act effectively only in physiological conditions of increased conductivity and temperature range of 30-40° C. In such conditions, the purified protein is exposed to the degrading activity of proteases present in the sample, which even in residual amounts might have a detrimental effect on protein integrity.

Citation or identification of any document in this application is not an admission that such document is available as prior art to the present invention.

SUMMARY OF THE INVENTION

An object of the presented invention is to overcome the indicated disadvantages and to deliver a lytic enzyme with a glycylglycine endopeptidase activity active against Gram-positive bacteria, in particular S. aureus, which is effectively produced, stable, and provides a high specificity against the substrate and high activity in nonphysiological conditions of low salt concentration, which is effective in a wide range of temperatures, including low temperatures.

A further object of the invention is to provide a new tool useful in molecular biology in bacterial cell lysis and in the preparation of proteins such as cleaving off tags and proteins from fusion proteins.

The inventors have unexpectedly found that the stable and active form of an autolysin from S. aureus (LytM), in particular a fragment corresponding to the catalytic domain, overcomes the indicated disadvantages and is capable to effectively degrade the cell walls of Gram-positive bacteria, in particular S. aureus in an environment significantly different from the physiological conditions, in particular in low conductivity, low salt concentration and is effective over a wide range of temperatures, including low and high temperatures.

The essence of this invention is based on the fact that it is possible to use a stable form of LytM protein or derivatives thereof to cleave a peptidic substrate in the conditions of conductivity lower than 10 mS/cm, preferably in conditions of conductivity below 2 mS/cm, over a wide range of temperatures.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

(squares), 8.0 (circles) and 9.0 (triangles), respectively. *S. aureus* cells were collected in the exponential growth phase, washed and resuspended in the test buffer to an apparent $OD_{595}$~1.8. The addition of $LytM_{185-316}$ or lysostaphin (both at 18 mM final concentration) led to cell lysis, which reduced light scattering and thus apparent $OD_{595}$. As some decrease of OD was also observed in the absence of enzyme, all $OD_{595}$ values were expressed as percent of the control without enzyme.

Figure 6:
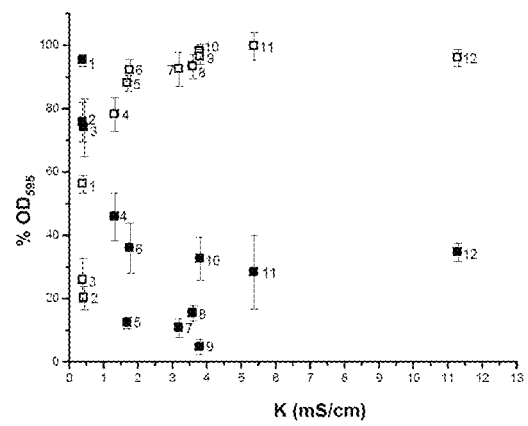

FIG. 6 illustrates the effect of various buffers on lytic activity in vitro of $LytM_{185-316}$ (open squares) and lysostaphin (closed squares). The lysis was carried out in the following buffers: (1) dd water, (2) glycine-NaOH, (3) D,L-alanine-NaOH, (4) diglycine-NaOH, (5) bicine-NaOH, (6) triglycine-NaOH, (7) Tris-HCl, (8) Hepes-NaOH, (9) phosphate buffer, (10) L-arginine-HCl, (11) L-glutamic acid-NaOH, (12) diaminopimelic acid-NaOH. All buffers were 50 mM with pH adjusted to 8.0 and data were collected after 60 min of reaction. The conductivity of the buffers was measured at room temperature after addition of *S. aureus* cells.

Figure 7:
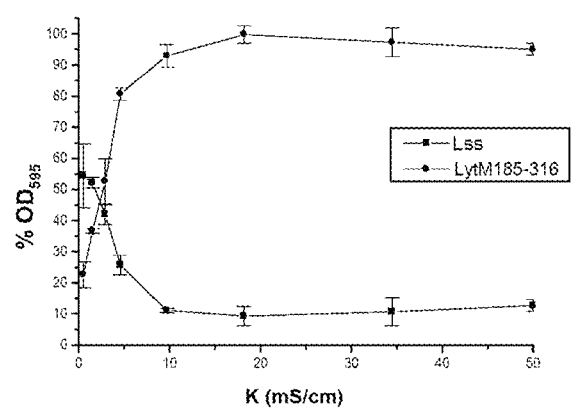

FIG. 7 illustrates the effect of ionic strength of the reaction buffer on the lytic activity of lysostaphin and $LytM_{185-316}$. The lysis was performed in standard conditions (Example 9b) in 20 mM glycine buffer pH 8.0 supplemented with 0 to 500 mM NaCl. Conductivity of the reaction was measured at room temperature after addition of *S. aureus* cells. Presented results were collected after 60 min. of lysis reaction at 37° C.

Figure 8:
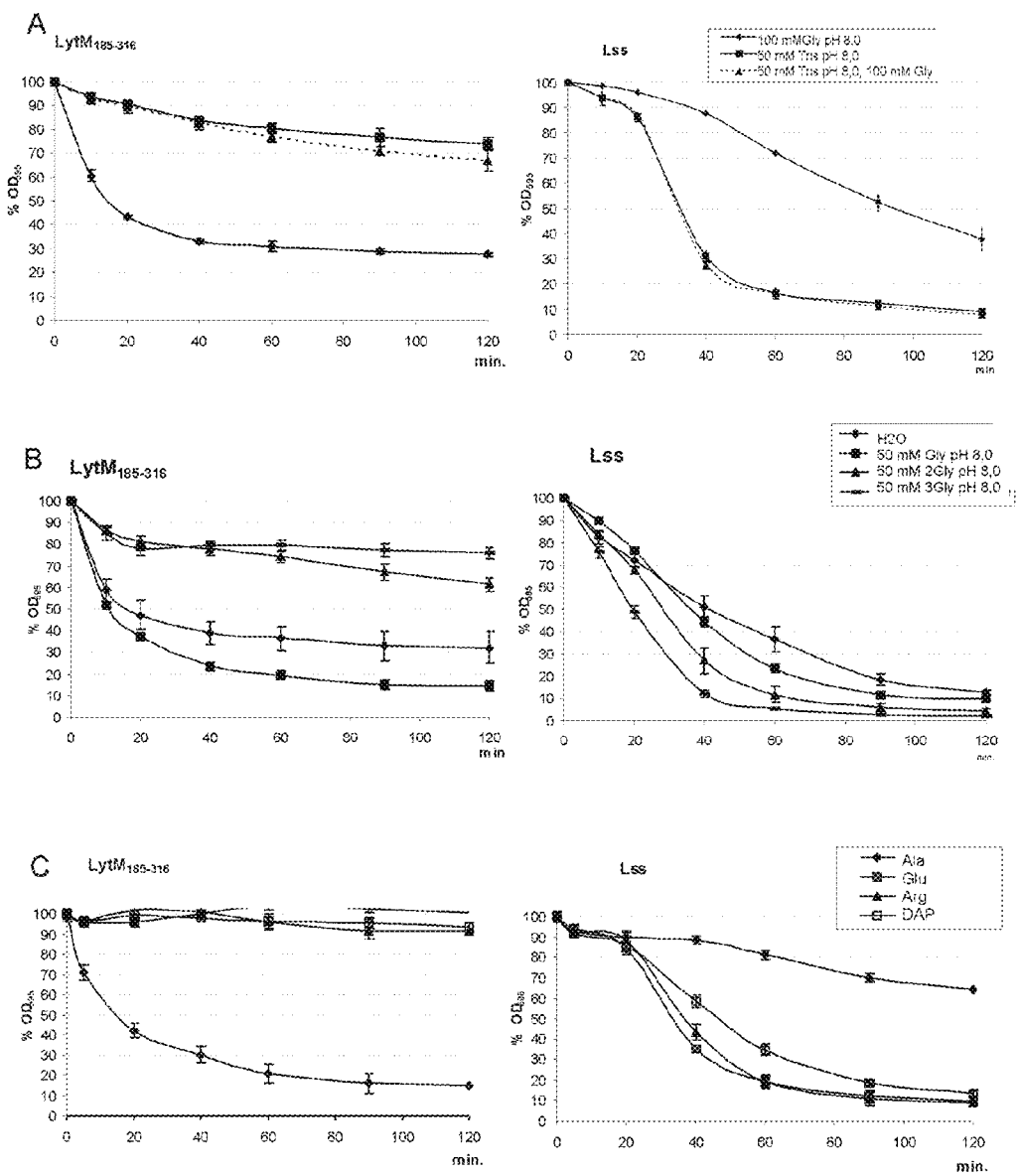

FIG. 8 illustrates the effect of various reaction conditions on the lytic activity of lysostaphin and $LytM_{185-316}$. (A) Effect of glycine. Lysis experiments were done in 100 mM glycine-NaOH, pH 8.0 (Gly), 50 mM Tris-HCl, pH 8.0 and 100 mM glycine (Gly) in 50 mM Tris-HCl pH 8.0. (B) Effect of mono-(Gly) di-(2Gly) and triglycine (3Gly) in cell lysis. Buffers were made as 50 mM with pH adjusted to 8.0 using NaOH. For comparison lysis in dd water was also checked. (C) Effect of various amino acids. D,L-alanine-NaOH (Ala), L-arginine-HCl (Arg), L-glutamic acid-NaOH (Glu), (12) diaminopimelic acid (DAP)-NaOH of pH 8.0 were tested. Lysis experiments were performed as described in Example 8.

Figure 9:
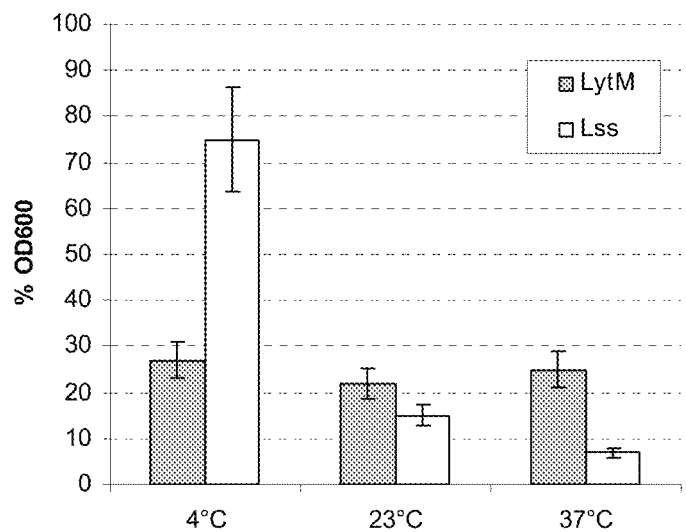

FIG. 9 illustrates comparison of the activity of the active form of LytM ($LytM_{185-316}$) and lysostaphin (Lss) in various temperatures. The results are presented as percent of the initial OD (% $OD_{600}$) of the cell suspension of *S. aureus*. The results were obtained for reactions carried out for 60 min. in buffers optimal for each enzyme in temperatures 4° C., 23° C. and 37° C.

Figure 10:
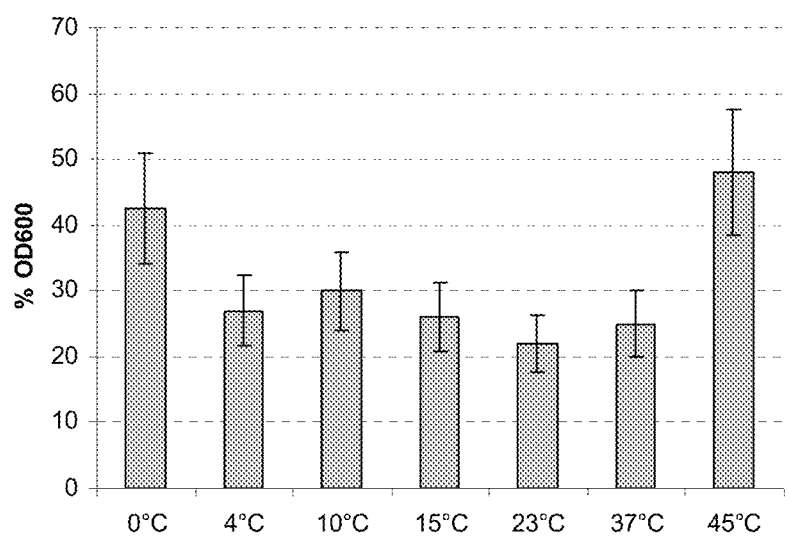

FIG. 10 illustrates activity of the active form of LytM at various temperatures. The results are presented as percent of the initial OD (% $OD_{600}$) of the cell suspension of *S. aureus*. The results were obtained for the reaction carried out for 60 min. in buffers optimal for each enzyme in temperatures 0, 4, 10, 15, 23, 37 and 45° C., respectively.

DETAILED DESCRIPTION OF THE INVENTION

According to this description the term "active form of LytM" refers to proteins, polypeptides, peptides or recombinant proteins, polypeptides, peptides of the sequence identical or highly homologous to the amino acid sequence of *Staphylococcus aureus* protein LytM from residue 185 to residue 316 sustaining characteristic glycylglycine endopeptidase activity of the catalytic domain $LytM_{185-316}$. The preferable active form of LytM is a fragment $LytM_{180-316}$ cleaved off from the full length LytM by trypsin, more preferable is $LytM_{185-316}$ or derivatives thereof. The active form of LytM has activity of glycylglycine endopeptidase against substrate, which is built of at least four glycines in a row. The active form of LytM demonstrates hydrolytic activity against interpeptide bridges in peptidoglycans of Gram-positive bacteria. It is obvious that some changes in amino acid sequence of the polypeptide or the nucleotide sequence encoding such polypeptide resulting in changes in amino acid sequence will not influence the activity of the polypeptide.

The term "derivative of the active form of LytM" or "derivative of the $LytM_{185-316}$", which is a catalytic domain, refers to polypeptides of the amino acid sequence identical or highly homologous to the sequence of the active form of LytM or $LytM_{185-316}$, for which the coding sequences have been changed by replacement, deletion, insertion, in a way that the activity of the derivative of the active form is not changed.

The term "highly homologous sequence" means that the sequence is homologous in at least 70%, preferably in at least 80%, more preferably in at least 90%, the most preferably in at least 95%.

According to this description a "peptide substrate" or a "protein substrate" for the active form of LytM should be understood as a peptide or a polypeptide or a protein built of or which may comprise at least four glycines in a row, which are recognized and cleaved by the active form of LytM. In particular the glycine bridges in Gram-positive bacteria peptidoglycans built of at least four or more glycines in a row are the peptide substrates for the active form of LytM. The peptide substrate or protein substrate can be fusion proteins which may comprise at least four glycines in a row in a linker region.

The Gram-positive bacteria which have at least four glycines in a row in their interpeptide bridges belong to genus *Staphylococcus*, among others species: *S. aureus*, *S. epidermidis*, *S. roseus*, *S. carnosus*, *S. lactis*, *S. saprophyticus* and to genus *Micrococcus*, such as *M. caseolyticus*, *M. candidans*, *M. naucinus*, *M. vernae*.

In the first aspect, the invention provides the method of peptide hydrolysis, in particular of the cell walls of Gram-positive bacteria, wherein the active form of LytM or derivatives thereof are contacted with a peptide substrate, preferably with the cell walls of Gram-positive bacteria, in aqueous environment of conductivity lower than 10 mS/cm, more preferably of conductivity lower than 2 mS/cm. The preferred active form of LytM is the polypeptide $LytM_{185-316}$ of sequence SEQ ID No:2 or derivatives thereof. In preferred method of peptide hydrolysis the contact is conducted in a temperature range from about 0° C. to about 45° C., more preferably in the range about 0-37° C., in particular below 10° C. Moreover, the pH of the reaction preferably ranges from about 6 to about 9, particularly in the range from about 7 to about 9. Preferably the Gram-positive bacteria are bacteria belonging to genus *Staphylococcus* or *Micrococcus*, more preferably species such as: *S. aureus*, *S. epidermidis*, *S. roseus*, *S. carnosus*, *S. lactis*, *S. saprophyticus* and *M. caseolyticus*, *M. candidans*, *M. naucinus*, *M. vernae*.

In the second aspect, the invention provides a composition for use as a bacteriostatic or bactericidal (e.g. as bacteriolytic) agent, particularly against Gram-positive bacteria, in particular against genus *Staphylococcus* or *Micrococcus*, wherein composition may comprise the active form of LytM or derivative thereof, and wherein the composition is for use in aqueous environment of conductivity lower than 10 mS/cm, preferably lower than 2 mS/cm. In preferred composition the active form of LytM is the polypeptide LytM$_{185-316}$ of sequence SEQ ID NO:2, or derivatives thereof. The preferred composition is for use to disinfect the surface and preferably is in the form of liquid, emulsion, gel, spray, lotion or wet wipes. The composition might be supplemented with a suitable carrier, preservative, flavor, buffer and other components useful in eliminating bacteria, in particular detergents, solvents, antibiotics, and bacteriocines.

In the third aspect, the invention also provides the use of a composition which may comprise the active form of LytM or derivatives thereof, as a bacteriostatic or bactericidal agent or to disinfect the surface, preferably against Gram-positive bacteria, in particular against genus *Staphylococcus* or *Micrococcus*, wherein such composition is used in aqueous environment of conductivity lower than 10 mS/cm, preferably lower than 2 mS/cm. In a preferred use of the composition the active form of LytM is the polypeptide LytM$_{185-316}$ of sequence SEQ ID NO:2 or derivatives thereof.

The invention also concerns a peptidase capable of cleaving cell walls of Gram-positive bacteria in an aqueous environment of conductivity lower than 10 mS/cm. The peptidase may comprise the amino acid sequence of SEQ ID NO:2 or derivatives thereof and demonstrates activity on peptidic substrate, in particular on interpeptide bridges built of at least four glycines in peptidoglycans of Gram-positive bacteria. The preferred peptidase is active in the reaction conditions of conductivity below 2 mS/cm. Moreover, the preferred peptidase is active in the temperature range from about 0° C. to about 45° C., more preferably in the range from about 0° C. to about 37° C., in particular below 10° C.

The invention also provides the use of the active form of LytM or derivatives thereof as a bacteriostatic or bactericidal agent in food industry, wherein the agent is used in the reaction condition of conductivity lower than 10 mS/cm, preferably lower than 2 mS/cm. The preferred active form of LytM is the polypeptide LytM$_{185-316}$ of sequence SEQ ID NO:2 or derivatives thereof. The agent is preferably used as an additive to human and animal food or to decontaminate the surfaces, preferably against the Gram-positive bacteria, in particular belonging to genus *Staphylococcus* or *Micrococcus*.

In the next aspect, the invention provides the use of the active form of LytM or derivatives thereof as a bacteriostatic or bactericidal agent in medicine, veterinary and diagnostics, wherein the agent is used in the reaction condition of conductivity lower than 10 mS/cm, preferably lower than 2 mS/cm. The preferred active form of LytM is the polypeptide LytM$_{185-316}$ of sequence SEQ ID NO:2, or derivative thereof. The agent is preferably used to disinfect the tools and equipment used in medicine, veterinary and diagnostics, in particular surfaces in hospitals and laboratories, preferably against Gram-positive bacteria, particularly belonging to genus *Staphylococcus* or *Micrococcus*.

In yet another aspect, the invention provides the use of the active form of LytM or derivatives thereof to isolate the cell components from Gram-positive bacteria in the reaction conditions of conductivity lower than 10 mS/cm, preferably lower than 2 mS/cm. The preferred active form of LytM is the polypeptide LytM$_{185-316}$ of sequence SEQ ID NO:2, or derivatives thereof. The isolation of the cell components is preferably carried out in the temperatures from about 0° C. to about 45° C., preferably in the range 0-37° C., more preferably below 10° C., particularly from bacteria belonging to genus *Staphylococcus* or *Micrococcus*, particularly to the group including *S. aureus, S. epidermidis, S. roseus, S. carnosus, S. lactis, S. saprophyticus* and *M. caseolyticus, M. candidans, M. naucinus, M vernae*.

The invention also provides the use of the active form of LytM or derivatives thereof in diagnostics of Gram-positive bacteria, particularly bacteria belonging to genus *Staphylococcus* or *Micrococcus* in the reaction conditions of conductivity lower than 10 mS/cm, preferably lower than 2 mS/cm, wherein the preferred active form of LytM is the polypeptide LytM$_{185-316}$ of sequence SEQ ID NO:2 or derivatives thereof.

In another aspect, the invention provides the use of the active form of LytM or derivatives thereof to impregnate or to coat the surface exposed to Gram-positive bacteria, wherein the conditions in which the active form of LytM or derivatives thereof is used as an impregnation or as a coating of a surface have the conductivity lower than 10 mS/cm, preferably lower than 2 mS/cm. Such preferred active form of LytM is the polypeptide LytM$_{185-316}$ of sequence SEQ ID NO:2 or derivatives thereof.

The inventions also provides kit for lysis of the Gram-positive bacteria which may comprise an active form of LytM or derivatives thereof, wherein the active form of LytM or derivatives thereof are used in an environment of conductivity lower than 10 mS/cm, preferably lower than 2 mS/cm. Such preferred active form of LytM is the polypeptide LytM$_{185-316}$ of sequence SEQ ID NO:2 or derivatives thereof. The lysis of bacterial cells is carried out to isolate the cell components from Gram-positive bacteria, in particular DNA, RNA, proteins, peptides, glycopeptides, lipids, cell elements and useful metabolites.

The active form of LytM or derivative thereof is being used in the method of preparing a protein by enzymatic cleavage of tag from a protein substrate, which is preferably a fusion protein. The fusion protein is a recombinant protein produced in an expression system from the introduced/ engineered nucleic acid in which the coding sequence of the protein is linked to the sequence coding a tag. The linker sequence is designed to encode recognition sequence for the specific protease used to cleave off the tag from the recombinant fusion protein. When the active form of LytM is used to cleave off the tag, the peptidic linker has to contain at least four or more glycines in a row.

In the next aspect, the invention provides a method of preparing a protein by enzymatic cleavage of tag from a protein substrate which is a fusion protein, said method which may comprise the following steps: a fusion protein is formed by linking a sequence encoding the protein with a sequence encoding the linker which has at least four or more glycines in a row, and in the next step cleaving off the fusion protein with the active form of LytM or derivatives thereof. The preferred active form of LytM is LytM$_{185-316}$ of sequence SEQ ID NO:2 or derivatives thereof. The second step of the method is preferably performed in conductivity lower than 10 mS/cm, preferably lower than 2 mS/cm and/or at a temperature in the range from about 0° C. to about 45° C., more preferably in the range of 0-37° C., in particular below 10° C.

The invention also provides the use of an active form of LytM or derivative thereof for cleavage of tag or protein(s) from a protein substrate, preferably from a fusion protein, in which the cleavage is in the linker region of protein substrate which may comprise at least four or more glycines in a row. Preferably, the active form of LytM is the LytM$_{185-316}$ of sequence SEQ ID NO:2 or derivatives thereof. Preferably cleavage is conducted in conductivity lower than 10 mS/cm, preferably lower than 2 mS/cm and/or in a temperature range from about 0° C. to about 45° C., more preferably in the range 0-37° C., in particular below 10° C.

The active form of LytM or derivatives thereof might be used as a bacteriostatic or bactericidal (e.g. bacteriolytic) agent in medicine, veterinary or diagnostics. The active form of LytM or derivative thereof is preferably used in the reaction conditions of conductivity lower than 10 mS/cm, preferably lower than 2 mS/cm. The preferred active form of LytM is LytM$_{185}$-316 of sequence SEQ ID NO:2 or derivatives thereof. The bacteriostatic or bactericidal agent which may comprise the active form of LytM is used against Gram-positive bacteria, preferably belonging to genus *Staphylococcus* or *Micrococcus*. Such a bacteriostatic or bactericidal agent is useful to disinfect the surfaces of tools and equipment used in medicine, veterinary and diagnostics, hospital and laboratory surfaces and as a surface active agent on surfaces which can be contaminated by bacteria. Such agent might be used alone or in combination with other components used to eliminate bacteria, particularly detergents, solvents, antibiotics, bacteriocines or other enzymes. While the agent is used in combination, such composition may further comprise a suitable carrier, stabilizer, buffer or other additives. The active form of LytM or derivatives thereof might be used as a bacteriostatic or bactericidal agent in a form of liquid, emulsion, gel, spray, lotion, wet wipes or alike.

The active form of LytM or derivatives thereof is used as a component for the diagnostics of certain species of Gram-positive bacteria, preferably belonging to genus *Staphylococcus* or *Micrococcus*, in particular such species as for example: *S. aureus, S. epidermidis, S. roseus, S. carnosus, S. lactis, S. saprophyticus* as well as *M. caseolyticus, M. candidans, M. naucinus, M. vernae*. The active form of LytM or derivatives thereof will preferably be used in conditions of conductivity lower than 10 mS/cm, more preferably lower than 2 mS/cm. The active form of LytM or derivatives thereof might be used as a tool to perform specific peptide hydrolysis of bacteria for direct diagnostic of bacterial species or strains as well as at the stage of preliminary cell lysis for further diagnostics with, for example, such methods as PCR, nucleic acid hybridization, immunological and immunofluorescent methods, ELISA, and methods based on cell components such as enzymatic assays and others.

The active form of LytM or derivatives thereof is used as a tool to disintegrate the cell walls of Gram-positive bacteria for example to isolate components from cells of Gram-positive bacteria in the reaction conditions of conductivity lower than 10 mS/cm, preferably lower than 2 mS/cm. The preferred active form of LytM is LytM$_{185-316}$ of sequence SEQ ID NO:2, or derivatives thereof. The isolation of the cellular components might be carried out in temperatures from about 0° C. to about 45° C., preferably in the range 0-37° C., in particular below 10° C. The active form of LytM or derivatives thereof is preferably used to isolate components from cells of genus *Staphylococcus* or *Micrococcus* in particular such species as for example: *S. aureus, S. epidermidis, S. roseus, S. carnosus, S. lactis, S. saprophyticus* as well as *M. caseolyticus, M. candidans, M. naucinus, M. vernae*. The disintegration of the bacterial cell walls in order to lyse the bacteria may be aided by the addition of detergents or other factors weakening the structure of the cell wall, such as other enzymes. The disintegration of the cell walls might also be carried out in order to release protoplasts, enable bacterial cell transformation, to isolate nucleic acids, proteins, peptides as well as useful metabolites such as long chain carbohydrates.

The active form of LytM or derivatives thereof, in particular LytM$_{185-316}$ or derivatives thereof, therefore is used in kits intended to disintegrate Gram-positive bacterial cell walls for example to isolate cell components of Gram-positive bacteria in reaction conditions of conductivity lower than 10 mS/cm, preferably lower than 2 mS/cm. Such kits are also covered by the invention.

The active form of LytM or derivative thereof is used as a bactriostatic or bactericidal agent in food industry. The active form of LytM or derivatives thereof is preferably used in the reaction conditions of conductivity lower than 10 mS/cm, preferably lower than 2 mS/cm. The preferred active form of LytM is the polypeptide LytM$_{185-316}$ of sequence SEQ ID NO:2, or derivatives thereof. The bacteriostatic or bactericidal agent which may comprise the active form of LytM is used against Gram-positive bacteria, preferably belonging to genus *Staphylococcus* or *Micrococcus*. Such a bacteriostatic or bactericidal agent is used as an additive to human or animal food, to disinfect the surfaces, which get in contact with food, in particular tools and equipment used in food industry as well as rooms that get in contact with food or intermediate products. The active form of LytM or derivatives thereof is in particular used in diary industry and diary products.

The active form of LytM or derivatives thereof is used to impregnate or to coat surfaces exposed to Gram-positive bacteria, wherein the environment in which it is used as an impregnation or a coating has the conductivity lower than 10 mS/cm, preferably lower than 2 mS/cm. The preferred active form of LytM is the polypeptide LytM$_{185-316}$ of sequence SEQ ID NO:2, or derivatives thereof. The active form of LytM may be conjugated or added to carriers like polymers, copolymers or nanocarriers such as nanoballs or nanotubes, for example carbon nanotubes. The coated or impregnated surfaces may concern various surfaces for example rooms, tools, machines, appliances, medical equipment, diagnostic equipment or laboratory equipment. Such surfaces impregnated or coated with a layer which may comprise the active form of LytM or derivatives thereof will act by the extended period of time as bacteriostatic or bactericidal agent on Gram-positive bacteria.

The active form of LytM or derivatives thereof is used as a bacteriostatic or bactericidal agent in cosmetics industry. The active form of LytM or derivatives thereof will preferably be used in the reaction conditions of conductivity lower than 10 mS/cm, preferably lower than 2 mS/cm. The preferred active form of LytM is the polypeptide LytM$_{185-316}$ of sequence SEQ ID NO:2 or derivatives thereof. The bacteriostatic or bactericidal agent which may comprise the active form of LytM is used against Gram-positive bacteria, preferably belonging to genus *Staphylococcus* or *Micrococcus*. Such a bacteriostatic or bactericidal agent is being used as an additive to cosmetics improving their microbiological quality, or as an additive to liquids, creams, emulsions and lotions or as an agent to disinfect surfaces or to disinfect surfaces of various appliances, like tools and equipment used in cosmetics industry.

The active form of LytM or derivatives thereof is a peptidase of a very high specificity against sequences of at least four or more glycines in a row. The sequences recognized by LytM are very rare in proteins. Moreover, the cleavage performed by the active form of LytM or derivatives thereof is very effective in conditions of low conductivity like lower than 10 mS/cm or even below 2 mS/cm over a wide range of temperatures from about 0° C. to about 45° C., more preferably in the range 0-37° C., in particular in low temperatures below 10° C. Therefore LytM can cleave the protein from a protein substrate even in conditions in which the activity of other proteases is suppressed. This advantage allows to use the active form of LytM or derivatives thereof in conditions in which degrading activity of contaminating proteases or other impurities is significantly reduced or their activity is negligible. The active form of LytM or derivatives thereof is used to cleave the protein from a protein substrate, preferably a fusion protein, in which the cleavage is in the place of linker of the protein substrate of sequence which may comprise at least four or more glycines in a row.

Figure 1:
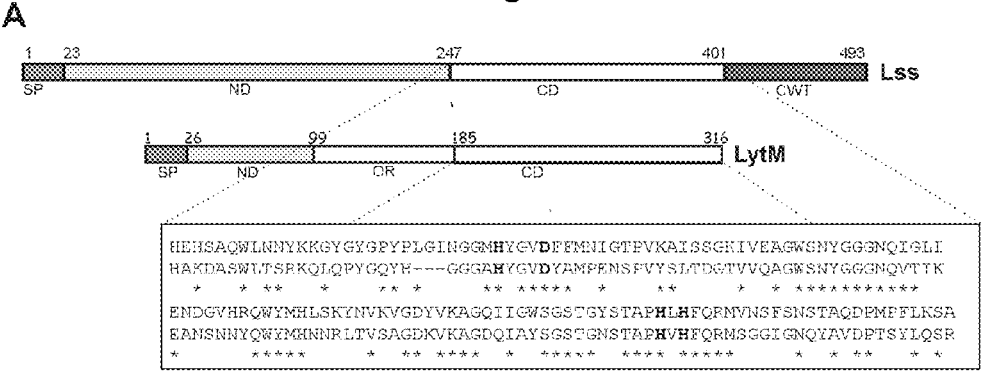
FIG. 1 (A) illustrates a schematic organization of the domains in the full length LytM and preprolysostaphin: SP—signal peptide, ND—N-terminal domain, OR—occluding region, CD—catalytic domain, CWT—cell wall targeting domain. Alignment shows significant similarity of these two proteins in the region of catalytic domain. Motifs $Hx_3D$ and HxH contain catalytic residues. Both amino acids, His and Asp, in the $Hx_3D$ motif as well as the second His in the HxH motif are ligands of $Zn^{2+}$. The first His of the HxH motif is located in the vicinity of $Zn^{2+}$ but it does not coordinate the ion. The variants of LytM with indicated (bold) residues mutated to alanines were tested. Mutant in which second His of the HxH motif was mutated to alanine could not be used because of insolubility. (B) illustrates schematic representation of lysostaphin (Lss), LytM and its fragments used in the examples of usage.
Figure 1:
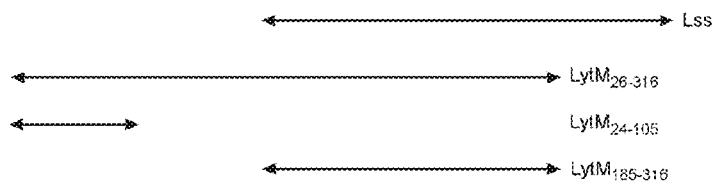
Figure 2:
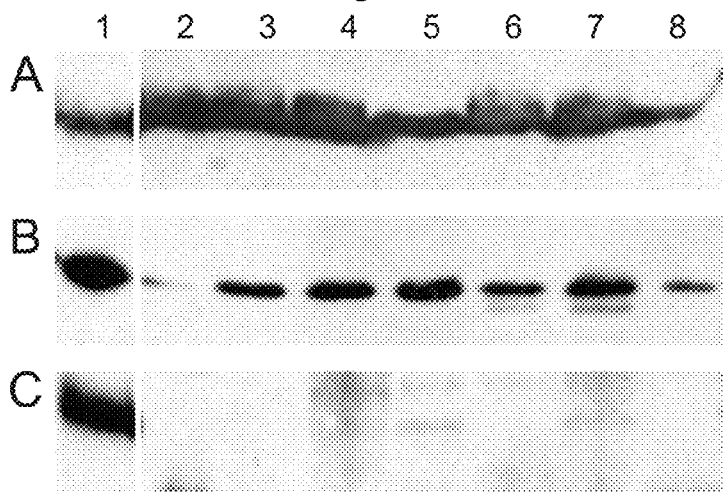
FIG. 2 illustrates results of the pull-down assay of (A) lysostaphin, (B) $LytM_{185-316}$ and (C) $LytM_{26-316}$ with S. aureus cell walls treated in various ways. (1) Input (control protein), (2) sonicated crude cell walls, (3) washed crude cell walls, (4) SDS-treated cell walls, (5) TCA-treated cell walls, (6) trypsinised cell walls, (7) purified peptidoglycans (8) commercially available peptidoglycans (Fluka). The proteins that were used as input (lane 1) or pulled down (lanes 2-8) were visualized by Western blotting with the anti-LytM antibodies.

The affinities of lysosatphin and LytM to different preparations of cell walls depleted of certain components (for example proteins, teichoic and lipoteichoic acids), as well as commercially available purified peptidoglycans were compared in the pull-down assay (FIG. 2). In all cases lysostaphin bound the cell wall preparations with various efficiencies (FIG. 2A). $LytM_{185-316}$ did not bind efficiently the sonicated, crude extracts of the cell walls. After additional washing of the cell walls, which probably removed the access of salts or/and eventually some inhibitors, the $LytM_{185-316}$ was efficiently bound in the pull-down assay. Further purification did not influence the binding significantly. These results indicate that $LytM_{185-316}$ binds the cell walls directly and interacts rather with peptidoglycans than with other components of the cell walls (FIG. 2B).

The role of various fragments of LytM in peptidoglycan binding was tested in the pull-down assay (FIG. 3A). The amounts of protein in the supernatant and in the bound fraction were compared indicating that the full length protein ($LytM_{26-316}$) does not bind peptidoglycans. The mutation of $Zn^{2+}$ ligand Asn117 to alanine should unblock the access to the active center of the catalytic domain but such a change had not significant influence on peptidoglycan binding. The isolated N-terminal domain ($LytM_{24-105}$) also did not bind peptidoglycans while the active form of LytM ($LytM_{185-316}$) was binding the peptidoglycans effectively. When two other $Zn^{2+}$ ligands H210 and D214 were separately mutated to alanines the protein lost the ability to bind. The exchange of the fourth $Zn^{2+}$ ligand, His293 from the motif HxH to alanine resulted in insoluble protein (Odintsov S. G. et al., 2004, J Mol Biol 335:775-85) what hindered the assay. The exchange of the first histidine His291 from the HxH motif to alanine resulted in less efficient but not completely abolished peptidoglycan binding.

Figure 3:
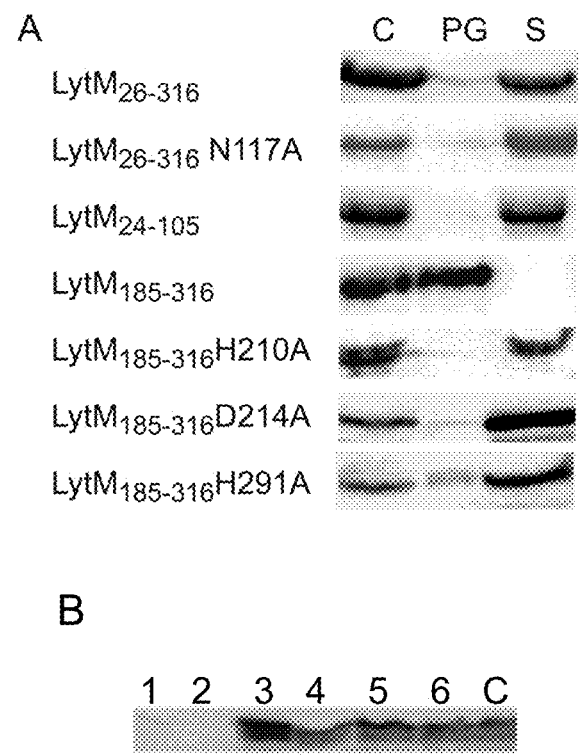
FIG. 3 illustrates results of the pull-down assay with purified peptidoglycans from S. aureus. (A) The full length LytM and its various fragments were analyzed by denaturing gel electrophoresis and Coomassie straining either directly (control, C) or after separation into peptidoglycan binding (PG) and supernatant (S) fractions. (B) $LytM_{185-316}$ was incubated with peptidoglycans in the presence of various protease inhibitors and the pellet fraction after pull-down was analyzed by denaturing gel electrophoresis and Western blotting with anti-LytM antibodies. (1) 10 mM EDTA, (2) 1 mM 1,10-phenantroline, (3) 10 mM N-acetylglucozamine, (4) 10 mM glycine hydroxamate, (5) 1 mM PMSF, (6) 1 mM E-64, (C) control without inhibitors.

The necessity of the active center integrity for the effective peptidoglycan binding was also confirmed by testing the effect of inhibitors. It was shown, that ion chelators inhibit binding of $LytM_{185-316}$ to peptidoglycans (FIG. 3B, lanes 1-2). However, the weak ion $Zn^{2+}$ chelator, glycine hydroxamate, and other protease inhibitors did not influence the peptidoglycan binding (FIG. 3B, lanes 3-6). The results show that the accessibility and integrity of the active center are necessary for the active binding of LytM protein to peptidoglycans (FIG. 3). The example of such an active form of LytM which has accessible active center with sustained integrity is $LytM_{180-316}$ generated by cleaving off the N-terminal domain and the occluding region from the full length LytM by trypsin, as well as the recombinant $LytM_{185-316}$ expressed in E. coli.

Both lysostaphin and $LytM_{185-316}$ bind pentaglycine interbridges in S. aureus peptidoglycans. Both proteins recognize interbridges as such, probably at least partially by interaction in the active site cleft. Lysosatphin has an additional domain binding the cell wall that provides specificity. Full length LytM and $LytM_{185-316}$ lack such a domain, therefore there was a possibility that the N-terminal domain of the full length protein plays such a role, especially in the light of observed high homology to SsaA (Staphylococcal secretory antigen A). However, the experiments disprove such a possibility, as neither the full length protein LytM nor separately generated N-terminal domain $LytM_{24-105}$ bind peptidoglycans.

The active form of LytM ($LytM_{185-316}$) binds the purified peptidoglycans more effectively while lysostaphin binds better to crude extracts, suggesting that lysostaphin also recognizes other components of the cell walls. Applicants have shown that the active form of LytM binds staphylococcal peptidoglycans directly and that it binds peptidoglycans washed with 20 mM Tris-HCl pH 7.5 that could remove access of salt and/or inhibitors more efficiently.

Applicants have shown that the active form of LytM, especially $LytM_{185-316}$, efficiently produced as a recombinant protein in E. coli, is very stable in the presence of staphylococcal proteases.

Applicants have shown that the externally applied active form of LytM effectively lyses living cells of Gram-positive bacteria, particularly S. aureus, by binding and lysing peptidic substrates of their cell walls in low conductivity conditions. The externally applied LytM was inhibiting the growth of staphylococci and acted as a bacteriostatic and bactericidal agent leading to the lysis of the S. aureus cells, what was proved in the conducted tests of cell lysis monitored by the changes of the optical density of cell suspension. The earlier experiments have shown only the ability of $LytM_{185-316}$ to digest tetra- and pentaglycine in experiments in vitro. It was not obvious that the active form of LytM applied externally to the solution of bacterial living cells will not be instantly degraded and will be able to effectively bind and degrade peptidic substrates in the cell walls of the living cells of S. aureus.

Figure 5:
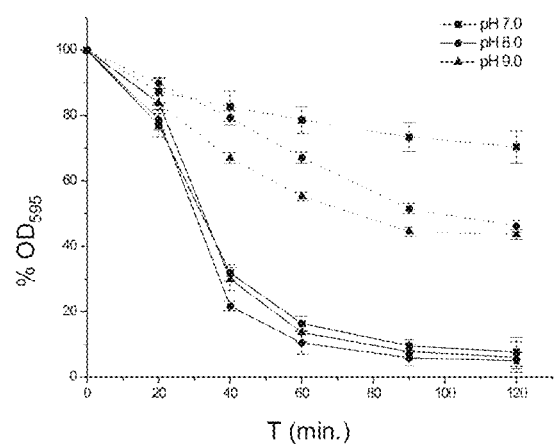
FIG. 5 illustrates the activity of lysostaphin (solid lines) and $LytM_{185-316}$ (dotted lines) in 50 mM Tris buffer at pH7.0

The activity of the peptidoglycan hydrolases was determined in the lysis tests of S. aureus cell walls by monitoring of the optical density changes of the cell suspension. An insignificant decrease of the optical density was observed also in the control without enzyme added, probably due to the residual enzymatic activity of the cell wall enzymes. Therefore, all values of OD at 595 nm are presented as a percent of the control. The value close to 100% indicates low activity while low percentage indicates high activity of the enzyme. Both lysostaphin and $LytM_{185-316}$ were only insignificantly effective at pH about 6 (50 mM phosphate buffer) but were more effective in pH about 7. Further increase of pH from 7 to 9 (50 mM Tris-HCl) had little influence on the activity of lysostaphin but had an impact on the increase of $LytM_{185-316}$ activity (FIG. 5). Applicants have shown that the active form of LytM acts efficiently in the rage of pH from about 6 to about 9, particularly in pH range from about 7 to about 9.

Unexpectedly, it turned out that the efficiency of the lysis of bacteria by the active form of LytM depends substantially on the reaction buffer. For example the activity of $LytM_{185-316}$ was higher in 20 mM than in 50 mM Tris-HCl (both at pH 8.0) and was even higher when Tris was replaced by glycine at pH 8.0. However, glycine does not act as an allosteric activator since it does not enhance the activity when is added in the presence of buffers of different composition. Similar results of dependence of activity on conductivity were also observed for buffers of different compositions (FIG. 8).

The lytic activity of $LytM_{185-316}$ and lysostaphin depends in an obvious way on buffer conductivity (FIG. 6); in low conductivity buffers degradation of S. aureus cell walls by lysostaphin is ineffective in contrast to $LytM_{185-316}$ which acts the best in low conductivity buffers while it is less efficient in high conductivity buffers.

The conductivity reflects both parameters, the concentration of ions and their mobility. The effect of conductivity on $LytM_{185-316}$ activity was tested in solutions of various ionic strength by changing the concentration of NaCl from 0 to 500 mM, The activity of lysostaphin and $LytM_{185-316}$ turned out to be dependent on ionic strength in a predicted way but the conductivity in this experiment was more directly correlated with ionic strength (FIG. 7).

The active form of LytM ($LytM_{185-316}$) acts in solutions with a low concentration of salt of conductivity of about 10 mS/cm corresponding approximately to a NaCl concentration of 100 mM. The preferred high activity of $LytM_{185-316}$ has been shown in the solutions of conductivity below 2 mS/cm corresponding to the approximate total concentration of ions of 15-20 mM for singly charged cations and anions of typical mobility, as well as in the double distilled water.

It has been shown that the active form of LytM is a stable protein acting efficiently over a wide range of temperatures from about 0° C. to about 50° C., particularly in the range from about 0° C. to 45° C., preferably in temperatures 0-37° C., more preferably 0-25° C., particularly in temperature below 10° C. Particularly surprising is the high activity of the active form of LytM in temperature about 4° C. in which $LytM_{185-316}$ is several times more active than lysostaphin.

The publications cited in the description with the references within are therefore all included as references.

The examples below are presented only to illustrate the invention and to explain certain aspect of it and not to limit the invention, therefore they should not be identified with its entire scope, which is defined in the enclosed claims.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Production of Various Forms of LytM Protein.

The fragments of DNA corresponding to $LytM_{24-105}$, $LytM_{185-316}$ and $LytM_{26-316}$ proteins were amplified by PCR from the previously described full length LytM clone (Odintsov et al., 2004, J. Mol. Biol. 335:775-785), inserted into the pET15mod vector and called $pET15modLytM_{24-105}$, $pET15modLytM_{185-316}$, $pET15modLytM_{26-316}$, respectively. Histidine tags were fused to an N-terminal part of the constructs coded for the LytM fragments. The coding sequence of $LytM_{185-316}$ was preceded by a Histag of the following sequence MGHHHHHHEF. The soluble forms of $LytM_{24-105}$, $LytM_{185-316}$ i $LytM_{26-316}$ were obtained by expressing the constructs in E. coli strain BL21(DE3) in the way described for $LytM_{185-316}$ in Odintsov S. G. et al., 2004, J. Mol. Biol. 335:775-785. Protein expression was induced during the logarithmic phase of the bacterial growth ($OD_{595}$ of 0.8) by the addition of 1 mM IPTG and continued for 4 h at 25° C. The recombinant protein was purified by affinity chromatography on a $Ni^{2+}$ loaded, nitrilo-triacetic acid (NTA) agarose column (Qiagen), followed by the gel filtration on a Sephacryl S200 column (Amersham Bioscience) according to manufacturer's description. In the examples presented below the stable, active form $LytM_{185-316}$ with Histag was used but no differences were observed in binding and activity of the active form LytM with and without Histag. The point mutants N117A, H210A, D214A, H291A, H293A were created by mutagenesis based on PCR using the Stratagene kit. All mutants were generated on vector $pET15modLytM_{185-316}$. The expression and purification of the mutated proteins were the same as for the protein $LytM_{185-316}$. Lysostaphin (mature form) used in the presented examples was purchased from Sigma and used without further purification.

Example 2

Generation of Polyclonal Anti-$LytM_{185-316}$ Antibodies.

Polyclonal antibodies against $LytM_{185-316}$ were raised in rabbit (Pineda Antibody Service, Berlin, Germany). Antibody purification was performed by affinity to $LytM_{185-316}$ protein coupled to CNBr-activated Sepharose 4B (Amersham Bioscience) according to the manufacturer's instructions. After washing, antibodies were eluted with 100 mM glycine pH 2.7. The pH of the eluant was immediately neutralised by the addition of 1/10 volume of 2 M Tris-HCl pH 8.0. The concentration of the antibodies in the eluant was estimated based on the absorption at $OD_{280}$.

Example 3

Generation of Cell Wall Fragments and Peptidoglycans from S. aureus

Late exponential phase cultures of S. aureus grown in CASO Broth medium at 37° C. were harvested by centrifugation, resuspended in buffer A (20 mM Tris-HCl pH 7.5) and autoclaved for 20 min. Crude extract was obtained after sonicating the cells for 3 min. The accessory wall polymers were removed by the following methods:

SDS treated walls were boiled in 4% SDS for 30 min.,
Trypsinized walls were prepared by 8 h trypsin digest (0.5 mg/ml) at 37° C.
Trichloroacetic acid (TCA) treatment was performed by 48 h incubation in 10% TCA at 4° C.,
Purified peptidoglycans were prepared as described previously Odintsov S. G. et al., 2004, J. Mol. Biol. 335:775-785 by combining all methods described above.

After each of these treatments, cell walls were extensively washed in 20 mM Tris-HCl pH 7.5.

Example 4

Binding of Various Forms of LytM and Lysostaphin to Peptidoglycans in the Pull-Down Assay To assess binding, 2 μg of protein produced in Example 1 and lysostaphin (Sigma) was mixed with cell walls or peptidoglycans (100 μg) produced in Example 3 and commercially available purified peptidoglycans (Fluka Biochemika, 77140) and incubated at room temperature for 15 min. Then, soluble and insoluble fractions were separated by centrifugation and peptidoglycans were washed with buffer 20 mM Tris-HCl pH 7.5, 50 mM NaCl. Soluble fractions and washed peptidoglycans were mixed with loading buffer and separated by SDS-PAGE. Proteins separated by SDS-PAGE were transferred onto ECL membrane (Amersham Bioscience) by semidry transfer and then incubated with 0.5 μg/ml purified antibodies against $LytM_{185-316}$ protein produced in Example 2. Goat anti-rabbit peroxidase-conjugated secondary antibodies (Sigma) were detected using Western Blot Luminol Reagent (Santa Cruz Biotechnology) according to manufacturer's recommendations. Lysostaphin was also recognised by the antibodies. The results are presented in FIG. 2. The active form of LytM (LytM$_{185-316}$) recognises different components of the call walls than lysostaphin—the affinity of lysostaphin and the active form LytM$_{185-316}$ was compared in the pull-down assay with various preparations of the cell walls from which different components, apart from peptidoglycans, were removed (FIG. 2).

The cell walls were used either crude (lane 2) or subjected to an extra washing step in 20 mM Tris-HCl pH 7.5 (lane 3), to SDS treatment, which should remove lipid components (lane 4), to TCA treatment, which is thought to remove teichoic acids (lane 5), or to trypsin treatment, which can be expected to remove protein components from the cell walls (lane 6). The pull-down assay was also carried out with "purified" peptidoglycan, which was obtained from crude cell wall preparations by a combination of the SDS-, TCA- and trypsin treatments (lane 7), and with purified peptidoglycan from a commercial source (Fluka Biochemika) (lane 8). In all cases, lysostaphin bound to the cell wall preparations albeit with different efficiency.

The obtained results show that binding of lysostaphin to crude extract was the most effective probably because of interactions between lysostaphin and non-peptidoglycan components of S. aureus cell walls (FIG. 2A). In contrast, LytM$_{185-316}$ was not effectively bound by sonicated extract without additional washing. However, when the cell walls were subjected to an additional washing step prior to the pull-down assay the LytM$_{185-316}$ was bound efficiently. This purification by washing in 20 mM Tris-HCl pH 7.5 could decrease the salt concentration in the reaction conditions but it's also possible that the potential inhibitory elements were removed from the sonicated cell walls. Further purification had little effect on the outcome of the pull-down assay.

Applicants have therefore shown that the active form LytM$_{185-316}$ interacts primarily with peptidoglycans rather than with other components of the cell walls (FIG. 2B). Full length LytM (without predicted signal peptide, LytM$_{26-316}$) was not efficiently pulled down by any of the peptidoglycan preparations. Traces of protein could be detected in the pull-down fraction in some cases but this effect was not specific because no systematic trend with increasing peptidoglycan purity was observed (FIG. 2C).

Example 5

Pull-Down Assay of Purified S. Aureus Peptidoglycans with Various Fragments of LytM.

To assess binding of various fragments of LytM, 2 μg of protein produced in Example 1 was mixed with purified peptidoglycans produced in Example 3 and incubated at room temperature for 15 min. Then, soluble and insoluble fractions were separated by centrifugation and peptidoglycans were washed with 1 ml of buffer A (20 mM Tris-HCl pH 7.5; 50 mM NaCl). Soluble fractions (S) and washed peptidoglycans (PG) were mixed with loading buffer separated by SDS-PAGE in presence of control (C) that was a tested LytM fragment.

Samples were separated by SDS-PAGE and stained with Coomassie according to the standard protocol. The results are presented on FIG. 3A. The results indicate that the full length LytM (LytM$_{26-316}$) as well as the isolated N-terminal domain of the enzyme LytM$_{24-105}$ does not bind the purified peptidoglycans. The only efficient binding could be observed for the active form of LytM (LytM$_{185-316}$). The affinity to peptidoglycans was also tested for mutants LytM$_{26-316}$ N117A and LYtM$_{185-316}$ H210A, D214A, H291A but it turned out that these mutants were binding peptidoglycans very weakly or completely lost the ability to bind. The results show that for the efficient binding of peptidoglycans the active form of LytM with sustained integrity of the active center is required.

Example 6

Pull-Down Assay of the Active Form of LytM in the Presence of Protease Inhibitors.

The test was carried out as in Example 4 but to check the effect of protease inhibitors on peptidoglycan binding the protein LytM$_{185-316}$ was incubated with purified peptidoglycans in presence of various inhibitors in the final concentrations: (1) 10 mM EDTA, (2) 1 mM 1,10-phenanthroline, (3) 10 mM N-acetylglucosamine, (4) 10 mM glycine hydroxamate, (5) 1 mM PMSF and (6) 1 mM E-64 a cystein protease inhibitor (trans-Epoxysuccinyl-L-leucylamido(4-guanidino)butane), (C) control without inhibitors. The results are presented in FIG. 3B. The obtained results indicate that the metal ion chelators, EDTA and 1,10-phenentroline, effect the binding of the active form LytM$_{185-316}$ to peptidoglycans (FIG. 3B, lanes 1-2) while the weak chelators of $Zn^{2+}$ ions, like glycine hydroxamate and protease inhibitors had no effect on peptidoglycan binding (FIG. 3B, lanes 3-6).

Example 7

Stability of the Active Form of LytM in the Presence of Bacterial Proteases

Figure 4:
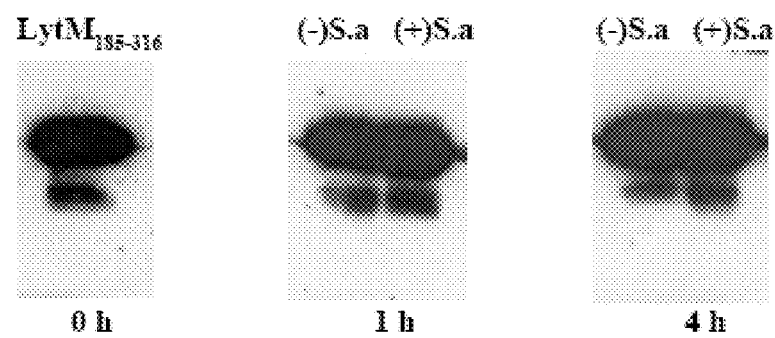
FIG. 4 illustrates the results of stability test of the active form $LytM_{185-316}$ in the presence of S. aureus cells and secreted staphylococcal proteases. The protein $LytM_{185-316}$ was incubated with cells of S. aureus ((+)S.A) or in the same conditions but without cells of S. aureus ((−) S.a.) for 1 hour (1 h) or 4 hours (4 h). The identical amount of protein $LytM_{185-316}$ not incubated at 37° C. (0 h) was used as a control. After incubation samples were electrophoretically separated on SDS-PAGE gels and visualized by Western blot hybridization with anti-LytM antibodies.

3 μg of LytM$_{185-316}$ obtained in Example 1 was incubated with ~$10^6$ cells of S. aureus for 1 and 4 hours at 37° C. LytM$_{185-316}$ not incubated at 37° C. was used as a control. After incubation the samples were separated by SDS-PAGE followed by Western blot hybridization with antibodies obtained in Sample 2 according to the method described in Example 4. The obtained results are presented in FIG. 4. The detected bands correspond to LytM$_{185-316}$. The lower band is present in all samples and its intensity does not differ between them. As such a band is detected in the control, its presence does not result from the LytM$_{185-316}$ degradation due to the presence of the S. aureus cells. Therefore, Applicants have shown the high stability of the acitve form LytM$_{185-316}$ in the presence of S. aureus cells.

Example 8

The Cell Wall Lysis Assay as Measured by the Optical Density Changes of the Cell Suspension (Turbidity Clearance Assay)

a) Effect of the pH on the Efficacy of the Active Form of LytM and Lysostaphin

The S. aureus cells grown on CASO media in 37° C. with shaking were harvested in the exponential phase, washed and suspended in the test buffer of 50 mM Tris pH 7.0 or 50 mM Tris pH 8.0 or 50 mM Tris pH 9.0 to OD$_{595}$ of about 1.8 supplemented with 200 μg/ml of erythromycin. LytM$_{185-316}$ obtained in the Example 1 and lysostaphin (Sigma) were added to the final concentration of 18 nM and 200 μl of the reaction mixture was transferred to microtiter plate. Plates were incubated at 37° C. with 2 second shaking every 5 minutes. The OD of the suspension was measured at 595 nm after 0, 20, 40, 60, 90 and 120 min of incubation. Because some decrease of OD in the control without enzyme was observed all values in FIG. 5 are presented as the percent of the control without enzyme. It has been demonstrated that the increase of pH in the range from about 7 to about 9 (50 mM Tris-HCl) had little effect on lysostaphin activity but enhanced the activity of $LytM_{185-316}$.

b) The Effect of the Buffer Conditions on the Efficacy of the Active Form of LytM and Lysostaphin.

The experiment was performed as in a) with the exception that the lysis reaction was performed (A) to check the effect of glycine on the reaction in the buffers of 100 mM glycine-NaOH pH 8.0, 50 mM Tris-HCl pH 8.0 and 100 mM glycine in 50 mM Tris HCl pH 8.0. (B) to check the effect of mono-, di- and triglycine on cell lysis in 50 mM buffers at pH adjusted to 8.0 with NaOH and in destilled water, (C) to check the effect of various amino acids: 50 mM L-arginine-HCl, D,L-alanine-NaOH, L-arginine-HCl, L-glutamic acid —NaOH, diaminopimelic acid-NaOH, all at pH 8.0. The obtained results are presented in FIG. 8. All tested buffers were of different composition but the same pH of 8.0.

The glycine buffer turned out to be the most preferable. Therefore, it has been checked whether the glycine alone might activate LytM as an additive to other buffers. The results indicate no such effect of glycine. Having in mind that the active form of LytM cuts the peptide bond between two glycines it has been checked as well if di- and triglycine have the same effect as the monoglycine. The results disapproved it. It has been shown that the activity of the acive form of LytM is highest in the buffer containing monoglycine and that it is not related to the LytM substrate. The high activity of $LytM_{185-316}$ was also observed in the double distilled water. The effect of several other amino acids on activity of $LytM_{185-316}$ was also tested. The activity varied in the tested solutions of amino acids but in none of them was as high as in glycine buffer. In order to reveal the relation between the buffer and the enzyme activity the physicochemical features of the reaction buffers and the activities of the enzyme described wherein were tested in Example 9.

Example 9

Effect of the Reaction Conditions and the Lytic Activity of LytM and Lysostaphin.

a) The Effect of Various Buffers

The S. aureus cells grown on CASO media at 37° C. with shaking were harvested by centrifugation in the exponential phase, washed and suspended in the 50 mM buffer at pH set to 8.0 or in double distilled water supplemented with 200 μg/ml erythromycin. Cells were diluted in the tested buffer to $OD_{595}$ of 1.8. $LytM_{185-316}$ obtained in Example 1 and lysostaphin (Sigma) were added to the final concentration of 18 nM and 200 μl of the reaction mix transferred to the microtiter plate. The plates were incubated at 37° C. with 2 second shaking every 5 minutes. In the beginning of the test the conductivity of the cells suspended in the suitable buffer or water were measured using conductivity meter MeteLab CDM230 (Radiometer Analytical, France). The conductivity measurements were done at room temperature after addition of the S. aureus cells.

The OD of the suspension was measured at the wavelength of 595 nm after 60 min. of reaction. The lytic activity is presented as a percent of the control $OD_{595}$ (samples the same as for the reaction but without enzyme added). The same reactions were done on living cells without erythromycin added. Each experiment was performed twice with four paralleles. The results are presented in FIG. 6. The same results were obtained for samples supplemented with erythromycin and without. Unexpectedly it turned out that the active form of LytM ($LytM_{185-316}$) is very effective in buffers of low conductivity while the degradation of the S. aureus cell walls by lysostaphin in the low conductivity conditions is inconsiderable.

The activity of the active form of LytM was particularly high in the reaction conditions of conductivity below 2 mS/cm and even in conditions of conductivity lower than 1 mS/cm. $LytM_{185-31}$ acts effectively also in double distilled water while lysostaphin activity was almost undetectable in such conditions.

b) The Effect of Ionic Strength of Buffer

The experiment was performed as in part a) with the exception that the lysis reaction was performed in 20 mM glycine buffer pH 8.0 supplemented with 0 to 500 mM NaCl. The results of the conductivity measurements are presented in FIG. 7. Applicants have shown that in contrast to lysostaphin the active form of LytM ($LytM_{185-316}$) is effective in low conductivity buffers, in particular in the reaction conditions of conductivity lower than 10 mS/cm, preferably lower than 5 mS/cm, more preferably lower than 2 mS/cm.

Example 10

Effect of the Temperature on Efficacy of the Active Form of LytM ($LytM_{185-316}$) and Lysostaphin (Lss)

The S. aureus cells grown on CASO media at 37° C. with shaking were harvested by centrifugation in the exponential phase and suspended in the 50 mM glycine buffer pH 7.5 for LytM and in the same buffer supplemented with 150 mM NaCl for lysostaphin to the final optical density of 1.8 at $OD_{595}$. $LytM_{185-316}$ obtained in Example 1 and lysostaphin (Sigma) were added to the final concentration of 18 nM (equal molar amounts) and 200 μl of the reaction mix was incubated in the tested temperatures for 60 min. After that changes in the optical density were measured at $OD_{595}$. The results shown in FIG. 9 and FIG. 10 are presented as a percent of the initial OD of the S. aureus cell suspension. The active form of LytM ($LytM_{185-316}$) was lysing bacteria over a wide range of temperatures from 0° C. to 45° C. At 4° C. $LytM_{185-316}$ is over four times more active than lysostaphin.

The list of sequences:

SEQ ID No:1 corresponds to the amino acid sequence of full length LytM from S. aureus SEQ ID No: 2 corresponds to the amino acid sequence of $LytM_{185-316}$ from S. aureus The invention is further described by the following numbered paragraphs:

1. A method of peptide hydrolysis comprising the step in which the active form LytM is contacted with peptide substrate, in aqueous environment of conductivity lower than 2 mS/cm, and wherein the active form LytM is at least 95% homologous to fragment $LytM_{180-316}$ which corresponds to residues 180-316 of sequence SEQ ID NO:1 or to $LytM_{185-316}$ of sequence SEQ ID NO:2; and wherein the active form LytM has glycylglycine endopeptidase activity of the catalytic domain $LytM_{185-316}$ which corresponds to residues 185-316 of sequence SEQ ID NO:1 against substrate, which is built of at least four glycines in a row.

2. The method of peptide hydrolysis according to paragraph 1, wherein the active form LytM is selected from fragment $LytM_{180-316}$ which corresponds to residues 180-316 of sequence SEQ ID NO:1 or $LytM_{185-316}$ of sequence SEQ ID NO:2.

3. The method of peptide hydrolysis according to paragraph 1 or 2, wherein the contacting is conducted in a temperature range from about 0° C. to about 37° C., preferably in temperature below 10° C.

4. A method of peptide hydrolysis of the cell walls of Gram-positive bacteria, wherein the active form of LytM is contacted with the cell walls of Gram-positive bacteria, in aqueous environment of conductivity lower than 2 mS/cm, and wherein the active form of LytM is at least 95% homologous to fragment LytM$_{180-316}$ which corresponds to residues 180-316 of sequence SEQ ID NO:1 or to LytM$_{185-316}$ of sequence SEQ ID NO:2; and wherein the active form LytM has glycylglycine endopeptidase activity of the catalytic domain LytM$_{185-316}$ which corresponds to residues 185-316 of sequence SEQ ID NO:1 against substrate, which is built of at least four glycines in a row.

5. The method of peptide hydrolysis according to paragraph 4, wherein the active form LytM is selected from fragment LytM$_{180-316}$ which corresponds to residues 180-316 of sequence SEQ ID NO:1 or LytM$_{185-316}$ of sequence SEQ ID NO:2.

6. The method of peptide hydrolysis according to paragraph 4 or 5, wherein the contacting is conducted in a temperature range from about 0° C. to about 37° C., preferably in temperature below 10° C.

7. The method of peptide hydrolysis according to paragraphs 4-6, wherein the Gram-positive bacteria are bacteria belonging to genus *Staphylococcus* or *Micrococcus*, more preferably species selected from group comprising: *S. aureus, S. epidermidis, S. roseus, S. carnosus, S. lactis, S. saprophyticus* and *M. caseolyticus, M. candidans, M naucinus, M. vernae*.

8. A use of a composition comprising the active form of LytM, as a bacteriostatic or bactericidal agent or to disinfect the surface, against Gram positive bacteria, in particular against the genus *Staphylococcus* or *Micrococcus*, wherein the composition is used in aqueous environment of conductivity lower than 2 mS/cm, and wherein the active form of LytM is at least 95% homologous to fragment LytM$_{180-316}$ which corresponds to residues 180-316 of sequence SEQ ID NO:1 or to LytM$_{185-316}$ of sequence SEQ ID NO:2, and wherein the active form LytM has glycylglycine endopeptidase activity of the catalytic domain LytM$_{185-316}$ which corresponds to residues 185-316 of sequence SEQ ID NO:1 against substrate, which is built of at least four glycines in a row.

9. The use of a composition according to paragraph 8, wherein, the active form of LytM is selected from active form of LytM which corresponds to residues 180-316 of sequence SEQ ID NO:1 or LytM$_{185-316}$ of sequence SEQ ID NO:2.

10. The use of a composition according to paragraphs 8-9, wherein the composition is used in the temperature below 10° C.

11. A use of the active form of LytM as bacteriostatic or bactericidal agent in food industry, wherein the agent is used in reaction conditions of conductivity lower than 2 mS/cm, and wherein the active form of LytM is at least 95% homologous to fragment LytM$_{180-316}$ which corresponds to residues 180-316 of sequence SEQ ID NO:1 or to LytM$_{185-316}$ of sequence SEQ ID NO:2, and wherein the active form LytM has glycylglycine endopeptidase activity of the catalytic domain LytM$_{185-316}$ which corresponds to residues 185-316 of sequence SEQ ID NO:1 against substrate, which is built of at least four glycines in a row.

12. The use according to paragraph 11, wherein the active form of LytM is selected from active form of LytM$_{180-316}$ which corresponds to residues 180-316 of sequence SEQ ID NO:1 or LytM$_{185-316}$ of sequence SEQ ID NO:2.

13. The use according to paragraphs 11-12, wherein the agent is used as an additive to human and animal food or to decontaminate surfaces.

14. The use according to paragraphs 11-13, wherein the agent is used against the Gram positive bacteria, preferably belonging to the genus *Staphylococcus* or *Micrococcus*.

15. The use according to paragraphs 11-14, wherein the agent is used in the temperature below 10° C.

16. A use of the active form of LytM as bacteriostatic and bactericidal agent in medicine, veterinary, diagnostics and/or in cosmetics industry, wherein the agent is used in the reaction conditions of conductivity-lower than 2 mS/cm, and wherein the active form of LytM is at least 95% homologous to fragment LytM$_{180-316}$ which corresponds to residues 180-316 of sequence SEQ ID NO:1 or to LytM$_{185-316}$ of sequence SEQ ID NO:2, and wherein the active form LytM has glycylglycine endopeptidase activity of the catalytic domain LytM$_{185-316}$ which corresponds to residues 185-316 of sequence SEQ ID NO:1 against substrate, which is built of at least four glycines in a row.

17. The use according to paragraph 16, wherein the active form of LytM is selected from active form of LytM which corresponds to residues 180-316 of sequence SEQ ID NO:1 or LytM$_{185-316}$ of sequence SEQ ID NO:2.

18. The use according to paragraphs 16-17, wherein the agent is used to disinfect the surface of tools and equipment used in medicine, veterinary, diagnostics and/or in cosmetics industry or to disinfect the surfaces in hospitals and laboratories.

19. The use according to paragraphs 16-18, wherein the agent is used against the Gram positive bacteria, preferably belonging to the genus *Staphylococcus* or *Micrococcus*.

20. The use according to paragraphs 16-19, wherein the agent is used in the temperature below 10° C.

21. A use of the active form of LytM, to isolate the cell components from Gram-positive bacteria comprising DNA, RNA, proteins, peptides, glycopeptides, lipids, cell elements and useful metabolites, in the reaction conditions of conductivity lower than 2 mS/cm, and wherein the active form of LytM is at least 95% homologous to fragment LytM$_{180-316}$ which corresponds to residues 180-316 of sequence SEQ ID NO:1 or to LytM$_{185-316}$ of sequence SEQ ID NO:2, and wherein the active form LytM has glycylglycine endopeptidase activity of the catalytic domain LytM$_{185-316}$ which corresponds to residues 185-316 of sequence SEQ ID NO:1 against substrate, which is built of at least four glycines in a row.

22. The use according to paragraph 21, wherein the active form of LytM is selected from active form of LytM which corresponds to residues 180-316 of sequence SEQ ID NO:1 or LytM$_{185-316}$ of sequence SEQ ID NO:2.

23. The use according to paragraphs 21-22, wherein the isolation of the cell components is carried out in temperature below 10° C.

24. The use according to paragraphs 21-23, wherein the Gram-positive bacteria are bacteria which belong to the genus *Staphylococcus* or *Micrococcus*, preferably species selected from the group comprising *S. aureus, S. epidermidis, S. roseus, S. carnosus, S. lactis, S. saprophyticus* and *M. caseolyticus, M candidans, M. naucinus, M. vernae*.

25. A use of the active form of LytM in diagnostics of Gram-positive bacteria, preferably bacteria belonging to the genus *Staphylococcus* or *Micrococcus* in the reaction conditions of conductivity lower than 2 mS/cm, and wherein the active form of LytM is at least 95% homologous to fragment LytM$_{180-316}$ which corresponds to residues 180-316 of sequence SEQ ID NO:1 or to LytM$_{185-316}$ of sequence SEQ ID NO:2, and wherein the active form LytM has glycylglycine endopeptidase activity of the catalytic domain LytM$_{185-316}$ which corresponds to residues 185-316 of sequence SEQ ID NO:1 against substrate, which is built of at least four glycines in a row.

26. The use according to paragraph 25, wherein the active form of LytM is selected from active form of LytM which corresponds to residues 180-316 of sequence SEQ ID NO:1 or LytM$_{185-316}$ of sequence SEQ ID NO:2.

27. The use according to paragraphs 25-26, wherein the active form of LytM is used in the temperature below 10° C.

28. A use of the active form of LytM to impregnate or to coat a surface exposed to Gram-positive bacteria, wherein the active form of LytM is at least 95% homologous to fragment LytM$_{180-316}$ which corresponds to residues 180-316 of sequence SEQ ID NO:1 or to LytM$_{185-316}$ of sequence SEQ ID NO:2, and wherein the active form LytM has glycylglycine endopeptidase activity of the catalytic domain LytM$_{185-316}$ which corresponds to residues 185-316 of sequence SEQ ID NO:1 against substrate, which is built of at least four glycines in a row, and wherein the condition in which said active form of LytM is used as an impregnation or as a coating of the surface has the conductivity lower than 2 mS/cm.

29. The use according to paragraph 28, wherein the active form of LytM is selected from active form of LytM which corresponds to residues 180-316 of sequence SEQ ID NO:1 or LytM$_{185-316}$ of sequence SEQ ID NO:2.

30. The use according to paragraphs 28-29, wherein the active form of LytM is used in the temperature below 10° C.

31. A method of preparing a protein by enzymatic cleavage of tag from a protein substrate that is a fusion protein, wherein the method comprises the following steps:

a) a fusion protein is formed by linking a sequence encoding the protein with a sequence encoding the linker which has at least four or more glycines in a row, b) cleaving the fusion protein with the active form of LytM, in conductivity lower than 2 mS/cm in a temperature range from about 0° C. to about 37° C., preferably in the temperature below 10° C., wherein the active form of LytM is at least 95% homologous to fragment LytM$_{180-316}$ which corresponds to residues 180-316 of sequence SEQ ID NO:1 or to LytM$_{185-316}$ of sequence SEQ ID NO:2, and wherein the active form LytM has glycylglycine endopeptidase activity of the catalytic domain LytM$_{185-316}$ which corresponds to residues 185-316 of sequence SEQ ID NO:1 against substrate, which is built of at least four glycines in a row.

32. The method according to paragraph 31, wherein the active form of LytM is selected from active form of LytM which corresponds to residues 180-316 of sequence SEQ ID NO:1 or LytM$_{185-316}$ of sequence SEQ ID NO:2.

33. A use of the active form of LytM for cleavage of a tag from the protein substrate, preferably from a fusion protein, wherein the cleavage is in the place of protein substrate of sequence comprising at least four or more glycines in a row and the cleavage is conducted in conductivity lower than 2 mS/cm in a temperature range from about 0° C. to about 37° C., preferably in the temperature below 10° C., and wherein the active form of LytM is at least 95% homologous to fragment LytM$_{180-316}$ which corresponds to residues 180-316 of sequence SEQ ID NO:1 or to LytM$_{185-316}$ of sequence SEQ ID NO:2, and wherein the active form LytM has glycylglycine endopeptidase activity of the catalytic domain LytM$_{185-316}$ which corresponds to residues 185-316 of sequence SEQ ID NO:1 against substrate, which is built of at least four glycines in a row.

34. The use according to paragraph 33, wherein the active form of LytM is selected from active form of LytM which corresponds to residues 180-316 of sequence SEQ ID NO:1 or LytM$_{185-316}$ of sequence SEQ ID NO:2.

* * *

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of peptide hydrolysis comprising a step in which the active form LytM is contacted with peptide substrate, in aqueous environment of conductivity lower than 2 mS/cm, and wherein the active form LytM is at least 95% homologous to fragment $LytM_{180\text{-}316}$ which corresponds to residues 180-316 of sequence SEQ ID NO:1 or to $LytM_{185\text{-}316}$ of sequence SEQ ID NO:2; and wherein the active form LytM has glycylglycine endopeptidase activity of the catalytic domain $LytM_{185\text{-}316}$ which corresponds to residues 185-316 of sequence SEQ ID NO:1 against substrate, which is built of at least four glycines in a row.

2. The method of peptide hydrolysis according to claim 1, wherein the active form LytM is selected from fragment $LytM_{180\text{-}316}$ which corresponds to residues 180-316 of sequence SEQ ID NO:1 or $LytM_{185\text{-}316}$ of sequence SEQ ID NO:2.

3. The method of peptide hydrolysis according to claim 1, wherein the contacting is conducted in a temperature range from about 0° C. to about 37° C.

4. A method of peptide hydrolysis of the cell walls of Gram-positive bacteria, wherein the active form of LytM is contacted with the cell walls of Gram-positive bacteria, in aqueous environment of conductivity lower than 2 mS/cm, and wherein the active form of LytM is at least 95% homologous to fragment $LytM_{180\text{-}316}$ which corresponds to residues 180-316 of sequence SEQ ID NO:1 or to $LytM_{185\text{-}316}$ of sequence SEQ ID NO:2; and wherein the active form LytM has glycylglycine endopeptidase activity of the catalytic domain $LytM_{185\text{-}316}$ which corresponds to residues 185-316 of sequence SEQ ID NO:1 against substrate, which is built of at least four glycines in a row.

5. The method of peptide hydrolysis according to claim 4, wherein the active form LytM is selected from fragment $LytM_{180\text{-}316}$ which corresponds to residues 180-316 of sequence SEQ ID NO:1 or $LytM_{185\text{-}316}$ of sequence SEQ ID NO:2.

6. The method of peptide hydrolysis according to claim 4, wherein the contacting is conducted in a temperature range from about 0° C. to about 37° C.

7. The method of peptide hydrolysis according to claim 4, wherein the Gram-positive bacteria are bacteria belonging to genus *Staphylococcus* or *Micrococcus*.

8. A method of isolating the cell components from Gram-positive bacteria comprising DNA, RNA, proteins, peptides, glycopeptides, lipids, cell elements and metabolites comprising administering the active form of LytM, to the Gram-positive bacteria, in the reaction conditions of conductivity lower than 2 mS/cm, and wherein the active form of LytM is at least 95% homologous to fragment $LytM_{180\text{-}316}$ which corresponds to residues 180-316 of sequence SEQ ID NO:1 or to $LytM_{185\text{-}316}$ of sequence SEQ ID NO:2, and wherein the active form LytM has glycylglycine endopeptidase activity of the catalytic domain $LytM_{185\text{-}316}$ which corresponds to residues 185-316 of sequence SEQ ID NO:1 against substrate, which is built of at least four glycines in a row.

9. The method according to claim 8, wherein the active form of LytM is selected from active form of LytM which corresponds to residues 180-316 of sequence SEQ ID NO:1 or $LytM_{185\text{-}316}$ of sequence SEQ ID NO:2.

10. The method according to claim 8, wherein the isolation of the cell components is carried out in temperature below 10° C.

11. The method according to claim 8, wherein the Gram-positive bacteria are bacteria which belong to the genus *Staphylococcus* or *Micrococcus*.

12. A method of preparing a protein by enzymatic cleavage of tag from a protein substrate that is a fusion protein, wherein the method comprises the following steps:
    a) a fusion protein is formed by linking a sequence encoding the protein with a sequence encoding a linker which has at least four or more glycines in a row,
    b) cleaving the fusion protein with the active form of LytM, in conductivity lower than 2 mS/cm in a temperature range from about 0° C. to about 37° C., wherein the active form of LytM is at least 95% homologous to fragment $LytM_{180\text{-}316}$ which corresponds to residues 180-316 of sequence SEQ ID NO:1 or to $LytM_{185\text{-}316}$ of sequence SEQ ID NO:2, and wherein the active form LytM has glycylglycine endopeptidase activity of the catalytic domain $LytM_{185\text{-}316}$ which corresponds to residues 185-316 of sequence SEQ ID NO:1 against substrate, which is built of at least four glycines in a row.

13. The method according to claim 12, wherein the active form of LytM is selected from active form of LytM which corresponds to residues 180-316 of sequence SEQ ID NO:1 or $LytM_{185\text{-}316}$ of sequence SEQ ID NO:2.

14. A method for cleaving a tag from a protein substrate, preferably from a fusion protein comprising administering the active form of LytM to the protein substrate, wherein the cleavage is in the place of protein substrate of sequence comprising at least four or more glycines in a row and the cleavage is conducted in conductivity lower than 2 mS/cm in a temperature range from about 0° C. to about 37° C., and wherein the active form of LytM is at least 95% homologous to fragment $LytM_{185\text{-}316}$ which corresponds to residues 180-316 of sequence SEQ ID NO:1 or to $LytM_{185\text{-}316}$ of sequence SEQ ID NO:2, and wherein the active form LytM has glycylglycine endopeptidase activity of the catalytic domain $LytM_{185\text{-}316}$ which corresponds to residues 185-316 of sequence SEQ ID NO:1 against substrate, which is built of at least four glycines in a row.

15. The method according to claim 14, wherein the active form of LytM is selected from active form of LytM which corresponds to residues 180-316 of sequence SEQ ID NO:1 or $LytM_{185\text{-}316}$ of sequence SEQ ID NO:2.

16. The method of claim 3, wherein the temperature is below 10° C.

17. The method of claim 6, wherein the temperature is below 10° C.

18. The method of claim 7 wherein the *Staphylococcus* genus comprises species *S. aureus, S. epidermidis, S. roseus, S. carnosus, S. lactis*, or *S. saprophyticus* and the *Micrococcus* genus comprises species *M caseolyticus, M candidans, M. naucinus*, or *M vernae*.

19. The method of claim 8 wherein the metabolites are long chain carbohydrates.

20. The method of claim 11 wherein the *Staphylococcus* genus comprises species *S. aureus, S. epidermidis, S. roseus, S. carnosus, S. lactis*, or *S. saprophyticus* and the *Micrococcus* genus comprises species *M caseolyticus, M. candidans, M naucinus*, or *M vernae*.

21. The method of claim 12, wherein the temperature is below 10° C.

22. The method of claim 14, wherein the temperature is below 10° C.

* * * * *

UNITED STATES PATENT AND TRADEMARK OFFICE
CERTIFICATE OF CORRECTION

PATENT NO. : 9,487,771 B2  
APPLICATION NO. : 14/056432  
DATED : November 8, 2016  
INVENTOR(S) : Izabela Sabala and Matthias Bochtler Page 1 of 1

It is certified that error appears in the above-identified patent and that said Letters Patent is hereby corrected as shown below:

On the Title Page

Item (71) Applicant:
Change "Warsaw" to --Warszawa--.

Item (73) Assignee:
Change "Warsaw" to --Warszawa--.

In the Claims

Column 25, Line 30:
Change "$185\text{-}316$" to --$185\text{-}316$--.

Column 26, Line 34:
Change "$185\text{-}316$" to --$180\text{-}316$--.

Column 26, Line 52:
Change "M caseolyticus" to --M. caseolyticus--.

Column 26, Line 52 to 53:
Change "M candidans" to --M. candidans--.

Column 26, Line 53:
Change "M vernae" to --M. vernae--.

Column 26, Line 59:
Change "M caseolyticus" to --M. caseolyticus--.

Column 26, Line 60:
Change "M naucinus, or M vernae" to --M. naucinus, or M. vernae--.

Signed and Sealed this  
Fourteenth Day of February, 2017

Michelle K. Lee  
*Director of the United States Patent and Trademark Office*

SEQUENCE LISTING

```
<160> NUMBER OF SEQ ID NOS: 2

<210> SEQ ID NO 1
<211> LENGTH: 316
<212> TYPE: PRT
<213> ORGANISM: Staphylococcus aureus

<400> SEQUENCE: 1

Met Lys Lys Leu Thr Ala Ala Ala Ile Ala Thr Met Gly Phe Ala Thr
1               5                   10                  15

Phe Thr Met Ala His Gln Ala Asp Ser Ala Glu Thr Thr Asn Thr Gln
            20                  25                  30

Gln Ala His Thr Gln Met Ser Thr Gln Ser Gln Asp Val Ser Tyr Gly
        35                  40                  45

Thr Tyr Tyr Thr Ile Asp Ser Asn Gly Asp Tyr His His Thr Pro Asp
    50                  55                  60

Gly Asn Trp Asn Gln Ala Met Phe Asp Asn Lys Glu Tyr Ser Tyr Thr
65                  70                  75                  80

Phe Val Asp Ala Gln Gly His Thr His Tyr Phe Tyr Asn Cys Tyr Pro
                85                  90                  95

Lys Asn Ala Asn Ala Asn Gly Ser Gly Gln Thr Tyr Val Asn Pro Ala
```

```
                100             105             110
Thr Ala Gly Asp Asn Asn Asp Tyr Thr Ala Ser Gln Ser Gln Gln His
            115             120             125
Ile Asn Gln Tyr Gly Tyr Gln Ser Asn Val Gly Pro Asp Ala Ser Tyr
        130             135             140
Tyr Ser His Ser Asn Asn Asn Gln Ala Tyr Asn Ser His Asp Gly Asn
145             150             155             160
Gly Lys Val Asn Tyr Pro Asn Gly Thr Ser Asn Gln Asn Gly Gly Ser
                165             170             175
Ala Ser Lys Ala Thr Arg Ser Gly His Ala Lys Asp Ala Ser Trp Leu
            180             185             190
Thr Ser Arg Lys Gln Leu Gln Pro Tyr Gly Gln Tyr His Gly Gly Gly
        195             200             205
Ala His Tyr Gly Val Asp Tyr Ala Met Pro Glu Asn Ser Pro Val Tyr
    210             215             220
Ser Leu Thr Asp Gly Thr Val Val Gln Ala Gly Trp Ser Asn Tyr Gly
225             230             235             240
Gly Gly Asn Gln Val Thr Ile Lys Glu Ala Asn Ser Asn Asn Tyr Gln
                245             250             255
Trp Tyr Met His Asn Asn Arg Leu Thr Val Ser Ala Gly Asp Lys Val
            260             265             270
Lys Ala Gly Asp Gln Ile Ala Tyr Ser Gly Ser Thr Gly Asn Ser Thr
        275             280             285
Ala Pro His Val His Phe Gln Arg Met Ser Gly Gly Ile Gly Asn Gln
    290             295             300
Tyr Ala Val Asp Pro Thr Ser Tyr Leu Gln Ser Arg
305             310             315

<210> SEQ ID NO 2
<211> LENGTH: 132
<212> TYPE: PRT
<213> ORGANISM: Staphylococcus aureus

<400> SEQUENCE: 2

His Ala Lys Asp Ala Ser Trp Leu Thr Ser Arg Lys Gln Leu Gln Pro
1               5               10              15
Tyr Gly Gln Tyr His Gly Gly Gly Ala His Tyr Gly Val Asp Tyr Ala
            20              25              30
Met Pro Glu Asn Ser Pro Val Tyr Ser Leu Thr Asp Gly Thr Val Val
        35              40              45
Gln Ala Gly Trp Ser Asn Tyr Gly Gly Gly Asn Gln Val Thr Ile Lys
    50              55              60
Glu Ala Asn Ser Asn Asn Tyr Gln Trp Tyr Met His Asn Asn Arg Leu
65              70              75              80
Thr Val Ser Ala Gly Asp Lys Val Lys Ala Gly Asp Gln Ile Ala Tyr
            85              90              95
Ser Gly Ser Thr Gly Asn Ser Thr Ala Pro His Val His Phe Gln Arg
        100             105             110
Met Ser Gly Gly Ile Gly Asn Gln Tyr Ala Val Asp Pro Thr Ser Tyr
    115             120             125
Leu Gln Ser Arg
    130
```